United States Patent
Li

(10) Patent No.: US 9,572,758 B2
(45) Date of Patent: Feb. 21, 2017

(54) METHOD OF MAKING HIGH PERFORMANCE ACTIVATED ALUMINUM SESQUICHLOROHYDRATE POWDERS

(71) Applicant: Gulbrandsen Technologies, Inc., Clinton, NJ (US)

(72) Inventor: Zijun Li, Westfield, NJ (US)

(73) Assignee: Gulbrandsen Technologies, Inc., Clinton, NJ (US)

( * ) Notice: Subject to any disclaimer, the term of this patent is extended or adjusted under 35 U.S.C. 154(b) by 0 days.

(21) Appl. No.: 14/755,138

(22) Filed: Jun. 30, 2015

(65) Prior Publication Data

US 2017/0000701 A1    Jan. 5, 2017

(51) Int. Cl.

| A61K 8/26 | (2006.01) |
|---|---|
| A61K 8/20 | (2006.01) |
| A61Q 15/00 | (2006.01) |
| C01F 7/56 | (2006.01) |
| A61K 8/02 | (2006.01) |
| A61K 8/04 | (2006.01) |
| A61K 8/44 | (2006.01) |

(52) U.S. Cl.
CPC .............. *A61K 8/26* (2013.01); *A61K 8/0229* (2013.01); *A61K 8/046* (2013.01); *A61K 8/44* (2013.01); *A61Q 15/00* (2013.01); *C01F 7/56* (2013.01); *A61K 8/20* (2013.01); *A61K 2800/30* (2013.01); *C01P 2002/87* (2013.01); *C01P 2006/82* (2013.01); *C01P 2006/90* (2013.01)

(58) Field of Classification Search
None
See application file for complete search history.

(56) References Cited

U.S. PATENT DOCUMENTS

| 4,359,456 | A | 11/1982 | Gosling et al. |
|---|---|---|---|
| 4,944,933 | A | 7/1990 | Inward |
| 5,718,876 | A | 2/1998 | Parekh et al. |
| 6,042,816 | A | 3/2000 | Shen |
| 6,902,724 | B1 | 6/2005 | Parekh et al. |
| 7,060,258 | B2 | 6/2006 | Li |
| 7,087,220 | B2 | 8/2006 | Li |
| 8,562,956 | B2 | 10/2013 | Pan |
| 8,883,129 | B2 | 11/2014 | Swaile et al. |

| 2006/0104918 | A1 | 5/2006 | Brown et al. | |
|---|---|---|---|---|
| 2007/0020211 | A1 | 1/2007 | Li et al. | |
| 2007/0196303 | A1* | 8/2007 | Li | A61K 8/26 424/68 |
| 2007/0286830 | A1* | 12/2007 | Li | A61K 8/26 424/68 |
| 2013/0209387 | A1* | 8/2013 | Pappas | A61K 8/26 424/66 |

FOREIGN PATENT DOCUMENTS

| EP | 0256832 A3 | 7/1988 |
|---|---|---|
| EP | 0274252 A1 | 7/1988 |
| EP | 0191628 A3 | 1/1990 |
| WO | 2013077832 A2 | 5/2013 |
| WO | 2014187685 A1 | 11/2014 |

OTHER PUBLICATIONS

L.F. Nazar, et al., "Speciation and Thermal Transformation in Alumina Sols: Structures of the Polyhydroxyoxoaluminum Cluster [Al30O8(OH)56(H2O)26]18+and its delta-Keggin Moiete", J. Am. Chem. Soc. 2000, 122, 3777-378.
Allouche et al., "Al30: A Giant Aluminum polycation", Agrew. Chem. 2000 112, 521-524.
Smart S. Vaughn J. Pappas I., Pan L. Controlled step-wise isomerization of the Keggin-type Al13 and determination of the gamma-Al13 structure. Chem Comm 2013; 49:11352-4.
Zijun Li, presentation given on Apr. 14, 2015, in Barcelona, Spain, at the in-cosmetics conference.
Extended European Search Report for Application No. EP16176430 dated Nov. 9, 2016.

* cited by examiner

*Primary Examiner* — Kevin S Orwig
(74) *Attorney, Agent, or Firm* — Lerner, David, Littenberg, Krumholz & Mentlik, LLP

(57) ABSTRACT

Activated aluminum sesquichlorohydrate (AASCH) powders and method of making are disclosed. The AASCH powder has Al:Cl atomic ratio of from about 1.60 to about 1.90 and Band III polymer concentration of at least about 20% and Band IV polymer concentration of at least about 15% when analyzed with Size Exclusion Chromatogram (SEC) operated by High Performance Liquid Chromatograph (HPLC). The method of making the active comprises (a) diluting the concentrated aluminum sesquichlorohydrate (ASCH) solution to from about 10% to about 25% by weight and (b) heating the diluted solution to obtain a Band III polymer concentration of at least about 20% and a Band IV polymer concentration of at least about 15%, and (c) drying the heated solution to powders having Al:Cl ratio of about 1.60 to about 1.90 and (d) optionally screen or light mill the powders to free flowing spherical particles.

17 Claims, No Drawings

METHOD OF MAKING HIGH PERFORMANCE ACTIVATED ALUMINUM SESQUICHLOROHYDRATE POWDERS

BACKGROUND OF THE INVENTION

The most effective antiperspirant active for an aerosol formulation on the market today is activated aluminum chlorohydrate (AACH). The AACH powder has Al:Cl atomic ratio of greater than 1.90 and mostly about 2.0, and has Band III polymer concentration of at least 20% and Band IV polymer concentration of less than 10%, when analyzed by the size exclusion chromatogram (SEC) using a high performance liquid chromatograph (HPLC).

Antiperspirant stick formulations can use the more efficacious materials, such as activated aluminum zirconium salts. However, aerosol spray formulations cannot use the activated aluminum zirconium salts due to the safety concern of inhalation of zirconium compounds. Therefore, aerosol spray formulations use the active containing Al salts only.

U.S. Pat. No. 4,359,456 to Gosling et al. discloses an improved Al active material through the process of heating from 2.5% to 8.5% by weight of aluminum concentration to have Band III polymer concentration of at least 20%. It discloses that the presence of Al polymers of above 100 Angstroms is not necessary to provide the high efficacy. The improved Al active material, disclosed in Gosling et al., i.e. basic aluminum chloride, has Al:Cl atomic ratio from about 0.5 to about 3.3. However, the salts having the Al:Cl ratio above 2.1 are not considered to have any antiperspirant properties, and therefore are not classified as conventional antiperspirant actives. Moreover, at lower Al:Cl ratio of about 0.5, it would be almost impossible to have at least 20% of Band III polymers.

U.S. Pat. No. 4,944,933 to Inward discloses a process of making a basic aluminum chloride in a powder form having Al:Cl atomic ratio of from 1.7 to 2.2 and having Band III polymer concentration of at least 20%. The process involves dissolving Al metal powder in aluminum chloride to form the final basic aluminum chloride solution of 7.5% to 13% by weight with reaction time being within 5 hours at 50° C.-105° C. and drying the BAC solution to powder. Even though the active salt prepared according to the process has high Band III polymer concentration, the Al polymer species, however are mostly $Al_{13}$ species characterized by $^{27}Al$ NMR having chemical shift at 62.5 ppm that provide low antiperspirant efficacy.

U.S. Pat. No. 5,718,876 to Parek et al. discloses basic aluminum halides and nitrates having enhanced antiperspirant efficacy that are produced by reacting aluminum metal with aluminum halide or nitrate solution at temperature greater than 85° C. with Al/anion ratio of about 1.2-1.8. The active solution has 30-400 of anhydrous weight having less than 20% of Band III polymers. Parek et al. discloses the concentrated Al sesquichlorohydrate solution with low amount of Band III polymers.

U.S. Pat. No. 8,883,129 to Swaile et al. discloses a method of making an active having enhanced antiperspirant efficacy comprising an Al-only salt having a Band III polymer concentration of at least 20% and no more than 20% of Al monomer. The method includes (a) making an aqueous solution of an aluminum salt having at least 20% of Band III polymers, (b) adding an aqueous solution of a monomeric aluminum salt to solution (a), and (c) rapidly drying the mixture to form a product. By minimizing the contact time between (a) and (b), Swalie et al. will maintain the monomeric state and acidity of the monomeric aluminum salt. The contact time varies from 1 second to 30 minutes depending on the temperature. Long contact time allows the monomeric aluminum salt to be neutralized by the aluminum hydroxychloride to form aluminum dimers, trimers and polymers. However, addition of very acidic aluminum chloride to diluted and activated aluminum solution will produce free acid upon spray drying that will not only corrode the spray dryer, but also cause the formation of colored specks, such as in black, brown, yellow and green colors. It will also generate the hygroscopic powder that is difficult to formulate. Specifically, if the active salt of Swaile et al. is formulated into an aerosol, the acidic and hygroscopic powder can corrode the orifice nozzle of the aerosol spray can, and also form larger agglomerates, clogging the orifice and preventing the spray from coming out of the aerosol can.

US patent application 2006/0104918 to Brown et al. discloses a suspension aerosol composition comprising milled AACH and a masking oil having reduced levels of white deposits. However, the very fine particles generated by milling process may pose health hazard for inhalation when used in an aerosol formulation.

Therefore, there is a need for a new and improved Al active material with enhanced antiperspirant efficacy for aerosol application, which is not too acidic and not too highly hygroscopic and/or does not pose safety concerns of inhalation of hazardous material.

BRIEF SUMMARY OF THE INVENTION

Described herein are activated aluminum sesquichlorohydrate (AASCH) with enhanced efficacy for aerosol application and method of making same.

In one embodiment, method of preparing an activated aluminum sesquichlorohydrate (AASCH) comprises (a) diluting the concentrated aluminum sesquichlorohydrate (ASCH) solution to about 10%-25% by weight, (b) heating the diluted solution to obtain a Band III polymer concentration of at least 20% and a Band IV polymer concentration of at least 15%, and (c) drying the solution to form a powder having Al:Cl ratio of about 1.60 to about 1.90. In another embodiment, the method further comprises (d) screening or light milling the powders to free flowing spherical particles having a particle distribution profile suitable for aerosol application.

In one embodiment, the diluted solution is heated until a Band III polymer concentration reaches above about 30%, and preferably above about 40%. In another embodiment, the diluted solution is heated until a Band IV polymer concentration reaches above about 20%, about preferably above about 30%. In another embodiment the diluted solution is heated to obtain a combined Band III and Band IV polymer concentration of at least about 40%, preferably at least about 50%.

In one embodiment, the drying is done via spray drying.

In one embodiment, the activated aluminum sesquichlorohydrate (AASCH) powders in accordance with the present invention have Al:Cl atomic ratio of from about 1.60 to about 1.90 and has a Band III polymer concentration of at least about 20% and a Band IV polymer concentration of at least about 15%. In one embodiment, the activated aluminum sesquichlorohydrate (AASCH) powders have at least about 50% of Band III polymer and Band IV polymer combined. In another embodiment, the AASCH powder has less than about 1% Band I polymer concentration. In yet another embodiment, the AASCH powders have no Band I polymer.

In yet another embodiment, the activated aluminum sesquichlorohydrate (AASCH) powder in accordance with the present invention has a Al species distribution that includes at least about 5% of $Al_{30}$, preferably at least about 10% of $Al_{30}$, more preferably at least about 15% of $Al_{30}$. In another embodiment, the activated aluminum sesquichlorohydrate (AASCH) powder in accordance with the present invention has an Al species distribution that includes less than about 10% of $Al_{13}$, preferably less than about 5% of $Al_{13}$, more preferably less than about 5% of $Al_{13}$.

In one embodiment, the activated aluminum sesquichlorohydrate (AASCH) powders in accordance with the present invention optionally contain a buffering agent. In other embodiments, the activated aluminum sesquichlorohydrate (AASCH) powders in accordance with the present invention do not contain any buffering agent.

DETAILED DESCRIPTION OF THE INVENTION

The invention will be described in more detail below.

While the specification concludes with the claims particularly pointing out and distinctly claiming the invention, it is believed that the invention described herein will be better understood from the following description. All temperatures are in degrees Celsius unless specified otherwise. The invention described herein can comprise (open ended) or consist essentially of the components of the invention described herein as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

It should be further understood that a description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

The term "concentration" used with respect to Band I, II, III, or IV polymer is used interchangeably with the term "amount". For example, a certain % of Band I polymer concentration is relative to the total concentration of Band I, II, III and IV. The concentration of Band I, Band II, Band III or Band IV polymers is analyzed by the size exclusion chromatogram (SEC) using a high performance liquid chromatograph (HPLC) as described hereinafter. A Phenomenex Column (3.9×300 mm, 10 um packing) and a Waters column (μPorasil Column 3.9×300 mm, 10 um packing) were connected in series to obtain a SEC-HPLC chromatograph. The HPLC employed is a Shimadzu RID 10A refractive index detector equipped with LC20 AD isocratic pump and 20 μL injector. For example, to measure the concentration of a specific Band polymer in activated aluminum sesquichlorohydrate (AASCH) powders, they were dissolved in DI water to form a 2% by weight Al solution and quickly injected into the HPLC and eluted at a flow rate of 0.9 mL/min with mobile phase of 0.01N nitric acid.

The highest molecular weight Al polymer species are eluted first designated as Band I. Band II and Band III are intermediate size Al complexes. Band IV is Al monomers and dimmers. The relative Band area of one or more peak is determined in order to characterize the distribution of polymeric species (e.g., Band I, II, III and IV) in the aluminum complexes formed.

The term "particle size" used herein is meant to refer to the volume mean diameter of the particles. The volume mean diameter is determined by laser light scattering using a Malvern-Mastersizer apparatus. A sample for analysis was prepared by adding a small amount of powder in a carrier medium. When the powder material is AASCH, isopropyl alcohol was used as the carrier medium.

Method

In one embodiment, the present invention provides a method for producing activated aluminum sesquichlorohydrate (AASCH) powders. In one embodiment, the method comprises diluting a concentrated aluminum sesquichlorohydrate (ASCH) solution of at least about 40% by weight to form a diluted ASCH solution of about 1% to about 25% by weight, preferably about 5 to about 20% by weight, more preferably from about 5 to about 15% by weight; heating the diluted ASCH solution to from about 85° C. to about 105° C. for at least about 30 minute, preferably at least about 60 minutes and most preferably at least about 90 minutes to form an activated aluminum sesquichlorohydrate (AASCH) solution; and drying the AASCH solution to form activated aluminum sesquichlorohydrate (AASCH) powders, wherein the AASCH powders have Al:Cl atomic ratio of from about 1.6 to about 1.9 and have a Band III polymer concentration of at least 20% and a Band IV polymer concentration of at least 15%.

We found that it is more difficult to activate basic aluminum chlorohydrate when Al:Cl ratio is below 1.5, i.e. less Band III and more acidic Al monomers will be formed. Further, upon drying the diluted aluminum sesquichlorohydrate solution after the heat treatment when the Al:Cl ratio is under 1.6, more acid is produced during spray drying. We found the lower the Al:Cl ratio of the feed solution, the more the free acid is produced. We also observed the AASCH powder having Al:Cl ratio below 1.6 contains lower Al content and more moisture, i.e. the lower the Al:Cl ratio the more hygroscopic the AASCH powder becomes. The more hygroscopic the AASCH powder, the more readily the powder absorbs the moisture from the environment to form larger agglomerate, thus easier to clog the orifice nozzle of aerosol can. By controlling Al:Cl ratio above 1.60, the AASCH powder will be less hygroscopic thus suitable for aerosol application. If the Al:Cl is more than 1.9, a Band IV polymer concentration is reduced to less than 10%, thus less Al monomers and dimers will be generated which would lead to lower antiperspirant efficacy.

The method may further comprise a step of sieving or milling the activated aluminum sesquichlorohydrate (AASCH) powders to obtain particles having an particle size from about 1 micron to about 200 microns, preferably from about 5 microns to about 150 microns and most preferably from about 10 microns to about 90 microns. Preferably, less than about 20% of the sieved or milled AASCH powders have a particle size under about 10 microns and 100% of the sieved or milled AASCH powders have particles size under about 120 microns.

In one embodiment, the diluted solution is heated to about 60° C. to about 110° C., preferably about 85° C. to about 100° C., and more preferably from about 90 to about 95° C. for from about 30 minutes to 5 hours, preferably from about 1 hour to 4 hours.

In one embodiment, the concentrated aluminum sesquichlorohydrate (ASCH) is prepared directly in the reactor through the reaction of Al metal with HCl or aluminum chloride. In another embodiment, the concentration ASCH is prepared by mixing 50% aluminum chlorohydrate (ACH) solution with HCl or basic polyaluminum chloride.

In one embodiment, the concentrated ASCH solution has Band I polymer concentration of less than 5% and Band III polymer concentration of less than 20%, but more than 0%. In another embodiment, the concentrated ASCH solution has Al:Cl atomic ratio of from about 1.5 to about 1.9. We found that it is more difficult to activate aluminum sesquichlorohydrate (ASCH) when Al:Cl ratio is below 1.5, i.e. less Band III and more acidic Al monomers will be formed. If the Al:Cl is more than 1.9, a Band IV polymer concentration is reduced to less than 10%, thus less Al monomers and dimers will be generated which would lead to lower antiperspirant efficacy.

The diluting of the concentrated aluminum sesquichlorohydrate (ASCH) solution may be done by adding any suitable solvent including, but not limited to water, propylene glycol, butylene glycol, 1,3-butane-diol, 1,4-butanediol, diethylene glycol, dipropylene glycol, tripropylene glycol, glycerin, sorbitol, or mixtures thereof.

In comparison to the activation of ACH solution, the activation of ASCH solution to form the AASCH takes less energy. Also, when the ASCH solution is activated, the Al species in the AASCH are further depolymerized demonstrated by high Band III and Band IV polymer concentration and low or no Band I polymeric species concentration compared to those in AACH.

In one embodiment, no acid or acidic aluminum chloride is introduced to the reaction solution after the heat treatment is completed. This is because either acid or aluminum chloride will produce free acid during the drying step, such as spraying drying, and may cause corrosion of the process equipment, such as spray dryer and milling equipment. Further the presence of the free acid in the drying and milling system will cause agglomeration of the dried activated powders. The combination of the corrosion of spray dryer and agglomeration of the dried activated powders will generate large colored specks such as black, brown, green and yellow colors.

In some embodiments, a buffering agent is introduced to the activated AASCH solution prior to the drying step. Suitable buffering agents include, without limitation, amino acids such as glycine, betaine, urea, alkaline and alkaline earth glycinate, zinc glycinate, calcium glycinate, strontium glycinate, and mixtures thereof. Examples of alkaline glycinate include, without limitation, lithium, sodium, potassium, ribudium, caesium and francium glycinates. Examples of alkaline earth glycinate include, without limitation, beryllium, magnesium, calcium, strontium, barium and radium. In some embodiments, the amount of a buffering agent present in the activated aluminum sesquichlorohydrate (AASCH) powder is from about 0.5% to about 10%, preferably from about 1% to about 5%.

The feed solution of the activated Al sesquichlorohydrate (AASCH) is preferably spray dried to a powder. The powder can be in the form of a particle. Most preferably most of the AASCH powders are spherical particles.

In order to be suitable for aerosol application, the powder is preferably to have less than 20% under 10 microns and 100% under 120 microns. In one embodiment, the pH of the AASCH powders range from about 3.0 to about 4.5, more preferably from about 3.5 to about 4.2. The pH is measured by dissolving the AASCH powders in D.I. water to form a 15% by weight solution.

AASCH Powders

In one embodiment, the present invention provides activated aluminum sesquichlorohydrate (AASCH) powders for aerosol application that has enhanced antiperspirant efficacy, leaves low or no white residue and does not corrode the aerosol can. In another embodiment, the AASCH powders have an Al:Cl atomic ratio of from about 1.60 to about 1.90 and have a Band III polymer concentration of at least about 20% and a Band IV polymer concentration of at least about 15%. Preferably, the atomic ratio of Al:Cl is from about 1.65 to about 1.85 and most preferably from about 1.70 to about 1.80.

The activated aluminum sesquichlorohydrate (AASCH) powders prepared according to the present invention comprise at least about 20%, and preferably at least about 30% and most preferably at least about 40% of Band III polymer. In one embodiment, the AASCH powders have a Band III polymer concentration of from about 20% to about 70%, preferably from about 20% to about 60%.

Moreover, the AASCH powders in accordance with the present invention have at least about 15%, preferably at least about 20%, and most preferably at least about 30% of Band IV polymer. In another embodiment, the AASH has a Band IV polymer concentration of from about 15% to about 50%, preferably from about 15% to about 40%.

Preferably, the AASCH powders in accordance with the present invention have less than about 1% Band I, more preferably no Band I polymers at all.

In yet another embodiment, the activated aluminum sesquichlorohydrate (AASCH) powders in accordance with the present invention have an Al species distribution that includes at least about 5% of $Al_{30}$, and preferably at least about 10% of $Al_{30}$. In another embodiment, the activated aluminum sesquichlorohydrate (AASCH) powder in accordance with the present invention has an Al species distribution that includes less than 10 of $Al_{13}$, and preferably less than about 5% of $Al_{13}$.

In yet another embodiment, the activated aluminum sesquichlorohydrate (AASCH) powders in accordance with the present invention have the moisture content of about 2% to about 15%, and preferably from about 3% to about 8%. The moisture content is measured by Infrared moisture balance (Mettler Toledo, model HB43). About 3 grams of the AASCH powders were employed for the moisture content measurement.

The activated aluminum sesquichlorohydrate (AASCH) produced by the method in accordance with the present invention has Al:Cl atomic ratio of from about 1.60 to about 1.90, preferably from about 1.65 to about 1.85 and most preferably from about 1.70 to about 1.80.

In one embodiment, the AASCH powder according to present invention has less white residue in comparison with AACH. Not wishing to be bound with theory, it is believed that the presence of more depolymerized Al species in AASCH will minimize the scattering of the light by the powder, thereby rendering the active less visible to the naked eye.

In some embodiments, a buffering agent may be included in the AASCH powder. Suitable buffering agents include, without limitation, amino acids such as glycine, betaine, urea, alkaline and alkaline earth glycinate, zinc glycinate, calcium glycinate, strontium glycinate and mixtures thereof. We found addition of glycine does not have much effect on Band III. Band IV, however is reduced. The same effect has been observed with zinc glycinate. In some embodiments, the amount of a buffering agent present in the activated aluminum sesquichlorohydrate (AASCH) powder is from about 0.5% to about 10%, preferably from about 1% to about 5%.

In other embodiments, the AASCH powder in accordance with the present invention does not contain any buffering agent, such as glycine. In yet another embodiment, the AASCH powder in accordance with the present invention is substantially free of zirconium.

In order to be suitable for aerosol application, the powder is preferably to have less than 20% under 10 microns and 100% under 120 microns. In one embodiment, the pH of the AASCH powders range from about 3.0 to about 4.5, more preferably from about 3.5 to about 4.2. The pH is measured by dissolving the AASCH powders in D.I. water to form a 15% by weight solution.

EXAMPLES

The following Examples illustrate some embodiments of the present invention. In the Examples, % Al and % Cl are by weight. % Band I, % Band III and % Band IV are peak areas, wherein % Band I+% Band II+% Band III+% Band IV=100%. Both 50% ACH and concentrated ASCH solutions are commercial solutions and manufactured by Gulbrandsen Technologies.

Example 1

50% aluminum chlorohydrate (ACH) solutions were mixed with basic polyaluminum chloride solutions to form a concentrated aluminum sesquichlorohydrate (ASCH) solution having various Al:Cl ratios ranging from 1.5 to 1.8. Then, water was added to dilute the concentrated aluminum sesquichlorohydrate (ASCH) solutions to 4.1% Al to 4.3% Al by weight, which corresponds to about 16.5% to about 17.4% by weight. The diluted solution is heated to about 90° C. to about 95° C. for about 2 hours to form an activated aluminum sesquichlorohydrate (AASH). The solutions were spray dried to powders. Table I below lists the characteristics of the resulting activated aluminum sesquichlorohydrate (AASH) powders.

TABLE I

| %Al | %Cl | Al:Cl Ratio | %M/C* | %Band I | %Band III | %Band IV |
|---|---|---|---|---|---|---|
| 23.05 | 18.98 | 1.60 | 10.11 | 0.00 | 23.46 | 31.29 |
| 24.10 | 18.78 | 1.69 | 8.92 | 0.00 | 27.35 | 29.19 |
| 24.04 | 18.29 | 1.73 | 8.57 | 0.81 | 32.18 | 15.34 |
| 24.09 | 18.07 | 1.75 | 8.14 | 0.93 | 34.40 | 19.36 |
| 24.71 | 17.83 | 1.82 | 7.12 | 0.97 | 36.44 | 14.64 |

*moisture content

Example 2

In Example 2, % Al concentrations of the feed solution were about 3.5% Al, which corresponds to 14% by weight, and the feed solution had various Al:Cl ratios ranging from 1.5 to 1.8. This set of experiment is directed to study the effect of concentration of the feed solutions on the SEC-HPLC Band profile. By comparing the results of Example 1 to Example 2, we found by decreasing the concentration of the feed solutions to 3.5% Al, Band III and Band IV peak areas are increased and Band I peak area is decreased as shown in Table II.

TABLE II

| %Al | %Cl | Al:Cl Ratio | %M/C | %Band I | %Band III | %Band IV |
|---|---|---|---|---|---|---|
| 23.44 | 19.95 | 1.54 | 11.62 | 0 | 35.55 | 41.32 |
| 23.9 | 17.92 | 1.75 | 9.09 | 0 | 41.77 | 37.75 |
| 24.7 | 17.35 | 1.87 | 7.96 | 0 | 40.77 | 33.74 |

Example 3

Different amount of glycine were added to the diluted and heated AASCH solutions and the solutions were spray dried. One of the case, glycine was not added. Compared with the AASCH powders with no glycine, the AASCH powders with glycine showed reduced Band IV peak area.

TABLE III

| %Al | %Cl | Al:Cl Ratio | %Glycine | %M/C | %Band I | %Band III | %Band IV |
|---|---|---|---|---|---|---|---|
| 23.35* | 17.90 | 1.71 | 3.9 | 9.12 | 0 | 53.58 | 20.73 |
| 23.12 | 17.60 | 1.73 | 3.9 | 9.12 | 0 | 41.28 | 20.61 |
| 23.69 | 17.93 | 1.74 | 0 | 8.76 | 0 | 41.63 | 30.23 |
| 23.69 | 17.93 | 1.73 | 4 | 8.17 | 0 | 39.24 | 25.35 |

*The concentration of the feed solution is 3.5% Al while the rest of the solution has 3.9% Al Example 4

Different amounts of zinc glycinate were added to the concentrated ASCH solution, followed by dilution and heat treatment. The resultant solutions were spray dried to powders and the results are demonstrated in Table IV.

TABLE IV

| %Al | %Cl | Al:Cl Ratio | %Glycine | %Zn | %Band I | %Band III | %Band IV |
|---|---|---|---|---|---|---|---|
| 23.25 | 17.75 | 1.72 | 2.85 | 0.70 | 0.23 | 36.36 | 20.11 |
| 23.68 | 18.00 | 1.73 | 4.78 | 1.16 | 0.32 | 37.36 | 20.56 |
| 23.29 | 17.81 | 1.72 | 6.67 | 1.61 | 0.92 | 36.41 | 20.41 |

Example 5

The scale ups at both pilot plant and large-scale production levels were conducted. For the pilot plant process, 8.25 Kg of ASCH solution was diluted with 22 Kg of water and the solution was heated until Band III was above 50%. The feed solution was then spray dried in pilot plant spray dryer at 250° C. inlet and 130° C. outlet temperatures to form the free flowing white powder.

For the production-scale process, 7766 Kg of ASCH solution and 19,000 Kg of water were mixed and heated until Band IV was higher than 50%. The solution was spray dried at 280° C. inlet and 130° C. outlet temperatures to the powder.

TABLE V

|  | %Al | %Cl | Al:Cl Ratio | %Band I | %Band III | %Band IV |
|---|---|---|---|---|---|---|
| pilot run | 24.14 | 18.35 | 1.73 | 0 | 49.61 | 22.00 |
| Production-scale | 25.12 | 18.31 | 1.80 | 0 | 49.92 | 19.69 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method of making activated aluminum sesquichlorohydrate (AASCH) powders consisting of:
   (a) diluting a concentrated aluminum sesquichlorohydrate (ASCH) solution to about 1% to about 25% by weight,
   (b) heating the diluted solution to activate the solution,
   (c) drying the activated solution to form the activated aluminum sesquichlorohydrate (AASCH) powders,
   (d) optionally adding a buffering agent prior to the drying, and
   (e) optionally sieving or milling the AASCH powders,
   wherein the activated AASCH powders have an Al:Cl ratio of from about 1.60 to about 1.90, a Band III polymer concentration of at least 20%, and a Band IV polymer concentration of at least 15%, wherein no acid or acidic aluminum chloride is introduced after the heating of the diluted solution.

2. The method of claim 1, wherein the Al:Cl ratio is from about 1.7 to about 1.8.

3. The method of claim 1, wherein the Band III polymer concentration is at least 40% and the Band IV polymer concentration is at least 20%.

4. The method of claim 1, wherein the buffering agent is selected from the group consisting of amino acid, alkaline glycinate, alkaline earth glycinate, zinc glycinate, strontium glycinate, and mixtures thereof.

5. The method of claim 1, wherein the buffering agent is selected from the group consisting of glycine, betaine, urea and mixtures thereof.

6. The method of claim 1, wherein the diluted solution is heated to about 85° C. to about 105° C. for at least 30 minutes.

7. The method of claim 1, wherein the diluting of the concentrated sesquichlorohydrate (ASCH) solution includes adding a solvent.

8. The method of claim 1, wherein the concentrated ASCH solution has a Band I polymer concentration of less than 5% and Band III polymer concentration of at least 20%.

9. The method of claim 1, wherein the concentrated ASCH solution has an Al:Cl ratio ranging from about 1.5 to about 1.9.

10. The method of claim 1, wherein the sieved or milled AASCH powders have a particle size ranging from about 1 micron to about 200 microns.

11. The method of claim 1, wherein the Band I polymer concentration is less than 1%.

12. The method of claim 1, wherein the AASCH powders are substantially free of zirconium.

13. The method of claim 1, wherein the drying is spray drying.

14. The method of claim 1, wherein the AASCH powders have at least 5% of $Al_{30}$.

15. The method of claim 1, wherein the AASCH powders have less than 10% of $Al_{13}$.

16. The method of claim 1, wherein the AASCH powders have a moisture content ratio ranging from about 2% to about 15%.

17. The method of claim 1, wherein the AASCH powders have a pH ranging from about 3.0 to about 4.5.

* * * * *